United States Patent

Steer

[11] Patent Number: 5,957,905
[45] Date of Patent: Sep. 28, 1999

[54] ORIFICE COUPLING

[75] Inventor: Peter L. Steer, East Grinstead, United Kingdom

[73] Assignee: Bristol-Myers Squibb Company, New York, N.Y.

[21] Appl. No.: 09/005,096

[22] Filed: Jan. 9, 1998

[30] Foreign Application Priority Data

Jan. 17, 1997 [GB] United Kingdom .................... 9700914

[51] Int. Cl.⁶ ........................................ A61F 5/44
[52] U.S. Cl. ............................................ 604/338; 604/342
[58] Field of Search .................................. 604/338, 339, 604/332, 342; 215/279

[56] References Cited

U.S. PATENT DOCUMENTS 5,647,861  7/1997  Steer et al. .............................. 604/342

*Primary Examiner*—Robert A. Clarke
*Assistant Examiner*—Catherine Cogut
*Attorney, Agent, or Firm*—Stuart E. Krieger

[57] ABSTRACT

An orifice coupling, e.g. an ostomy coupling, includes a first coupling part (10) securable to a second coupling part (20) by a springy split locking ring (30). The locking ring (30) is held captive on the first coupling member (10) by lugs (13) extending radially from outside the locking ring and which enable the locking ring (30) to engage the second coupling member (20) substantially continuously around the periphery of the second coupling member. The coupling can be released when the ends (26,27) of the locking ring (30) are manipulated to expand the ring. The locking ring (30) may be integrally moulded with the first coupling member, and folded into an operative position on the first coupling member.

15 Claims, 2 Drawing Sheets

ORIFICE COUPLING

BACKGROUND OF THE INVENTION

This invention relates to an orifice coupling. The invention is particularly suitable for use in the ostomy field, but is not limited exclusively to this field.

Ostomy couplings are used to connect and disconnect a bag for receiving a stomal discharge to and from a medical grade adhesive pad or base which is applied to the peristomal area of the skin of the wearer.

Many designs of ostomy coupling are known. In particular, EP-A-0737459 describes such a coupling in which first and second coupling members are held together by a springy flexible split locking ring. A plurality of tabs symmetrically arranged on each limb of the locking ring project through apertures in a rim of the first coupling member to retain the locking ring captive on the first coupling member, the tips of the tabs being engageable with the second coupling member through the apertures to secure the coupling members together. The tabs can be withdrawn generally radially outwardly by movement of the locking ring to permit separation of the two coupling members. This is achieved by applying an external force to the limbs of the split ring, to deform the limbs and thereby expand the ring.

SUMMARY OF THE INVENTION

In contrast to the prior art, the present invention provides, in a first aspect, a coupling in which first and second coupling members surrounding an orifice are securable together by a springy split locking ring captive on the first coupling member, the split locking ring being configured to engage the second coupling member substantially continuously around the periphery of the second coupling member, and to release said engagement with the second coupling member when external force is applied to the limbs of the split locking to expand the ring.

With such an arrangement, the locking ring can engage the second coupling member over a much greater area than in the prior art, and can therefore provide more positive engagement.

The locking ring need not engage the second coupling member at every single point around the periphery. In the preferred embodiment, the locking ring includes a continuous first engagement region on one limb, and a continuous second engagement ring on the second limb, which together, in use, leave a small region of the circumferential periphery of this coupling member unengaged. The unengaged region is at the "hinge" or pivot point of the locking ring, which is diametrically opposite the "split" in the ring and is the region where no, or only little, radial movement occurs when the ring is deformed.

In a second aspect, the invention provides a coupling in which first and second coupling members surrounding an orifice are securable together by a springy split locking ring on the first coupling member and which is engageable with the second coupling member, the first coupling member comprising retaining means extending radially outside the split ring for retaining the split ring on the first member, the retaining means permitting expansion of the split ring when an external force is applied to the limbs of the split ring, for releasing engagement with the to second coupling member and permitting the coupling members to be separated.

With such an arrangement, the retaining means for retaining the split ring on the first coupling member can retain the ring from radially outside the ring. In other words, the retaining means does not have to be interposed between the split ring and the peripheral surface of the second coupling member. This can provide a greater engagement area between the split ring and the second coupling member. Advantageously (although not essential in this aspect), the split ring may be configured to engage the second coupling member substantially continuously around the periphery of the second coupling member.

In the preferred embodiment, the means for retaining the split ring on the first coupling member comprises one or more retaining lugs.

In a further aspect, the invention provides an a coupling in which first and second coupling members surrounding an orifice are securable together by a springy split locking ring which is integral with a first of the coupling members and is captive thereon, the ring being deformable in use by applying a force to the limbs of the split locking ring, to enable the coupling members to be separated.

In a closely related aspect, the invention provides a method of producing a coupling member for use in a coupling according to the third aspect, the method comprising integrally moulding a coupling member and a split locking ring alongside and joined to the coupling member by a flexible web, and folding the web to superimpose the split locking ring on the coupling member.

Such a method provides a convenient technique for producing a coupling member with an attached split locking ring, and can provide more rapid and simple assembly than moulding the coupling member and the locking member separately. Preferably, the locking member is retained in its folded, operative state by one or more lugs projecting from the coupling member. A further preferred feature is that the flexible web joining the locking ring and the coupling member is diametrically opposed from the "split" or crossover region of the locking ring.

As defined herein, the term "split ring" is intended to cover any ring or partial ring member which functions, in use, as a ring with two limbs which can be moved apart and/or towards each other to expand and/or contract the ring.

Preferably, the coupling (of any aspect) is an ostomy coupling. One of the first and second coupling members would then form a body-side coupling member, and the other would form a bag-side coupling member.

An embodiment of the invention is now described by way of example only, with reference to the accompanying drawings, in which:

DETAILED DESCRIPTION OF THE INVENTION

Figure 1:
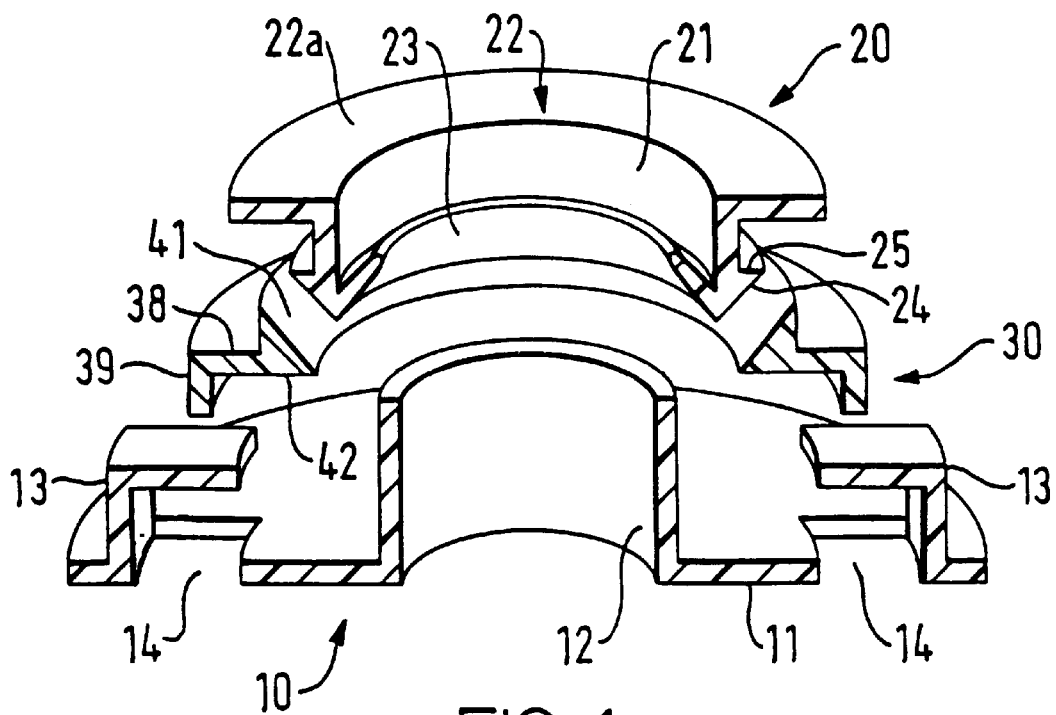
FIG. 1 is an exploded view showing the components of the coupling.

The illustrated and preferred ostomy coupling comprises first and second coupling members 10 and 20, and a split locking ring 30. In this embodiment, the first coupling member 10 is for attachment to a person's body and has a flange 11 from which projects a cylindrical wall 12 which surrounds the stomal orifice. The flange 11 is attached to a medical grade adhesive pad 15 (FIG. 3) which is preferably a thin film of polymeric material such as polyethylene and an adhesive layer situated on the rear surface of a base. Such an adhesive layer is preferably formed as a homogenious blenid of one or more pressure-sensitive viscous or elastomeric materials having intermittently dispersed therein one or more water-soluble or swellable hydrocolloid gums and may also include one or more thermoplastic elastomers and/or one or more swellable cohesive strengthening agents.

Figure 3:
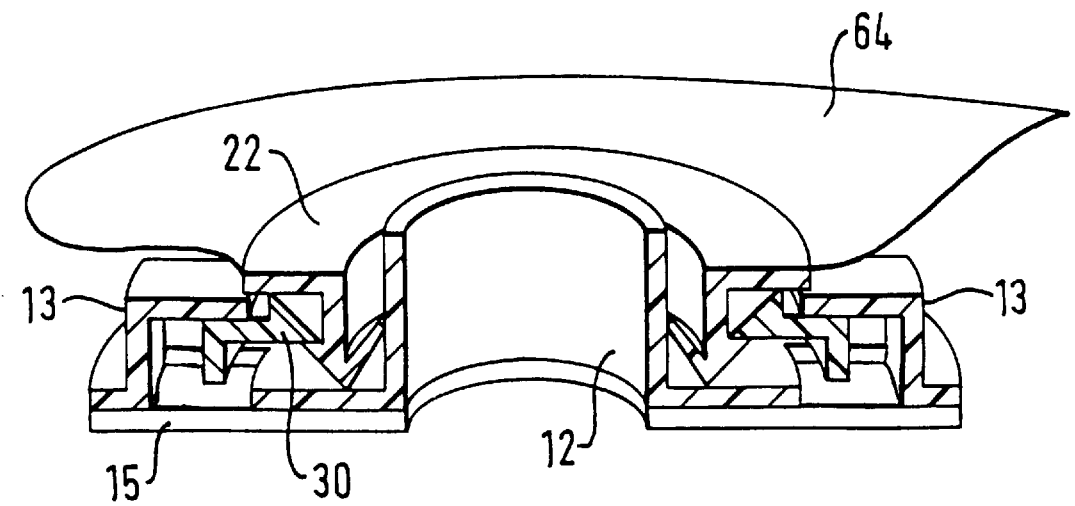
FIG. 3 is a vertical section through the coupling in the assembled condition.

Referring to FIGS. 1 and 3, the second coupling member is very similar to a conventional bag-side ostomy coupling member, and comprises a cylindrical wall 21 and a radially outwardly-extending flange 22. To the surface 22a of the flange 22, an ostomy pouch 64 is attached in any suitable manner, for example by adhesive. The cylindrical wall 21 is dimensioned to fit closely around the wall 12 of the first coupling member. A resilient seal strip 23 is integral with the cylindrical wall 21, and extends into contact with the wall 12 of the first coupling member 10 when the coupling is assembled. The function of the seal strip 23 (FIG.3) is to prevent leakage and to accommodate any minor tolerance variations which may have arisen in the moulding operation by which the coupling members 10 and 20 are manufactured.

Outside the seal strip 23, the external periphery of the cylindrical wall 21 is formed with an engagement profile for latching engagement with the locking ring 30. The engagement profile includes a radially ramped lead in surface 24, and an annular abutment surface 25.

Figure 2:
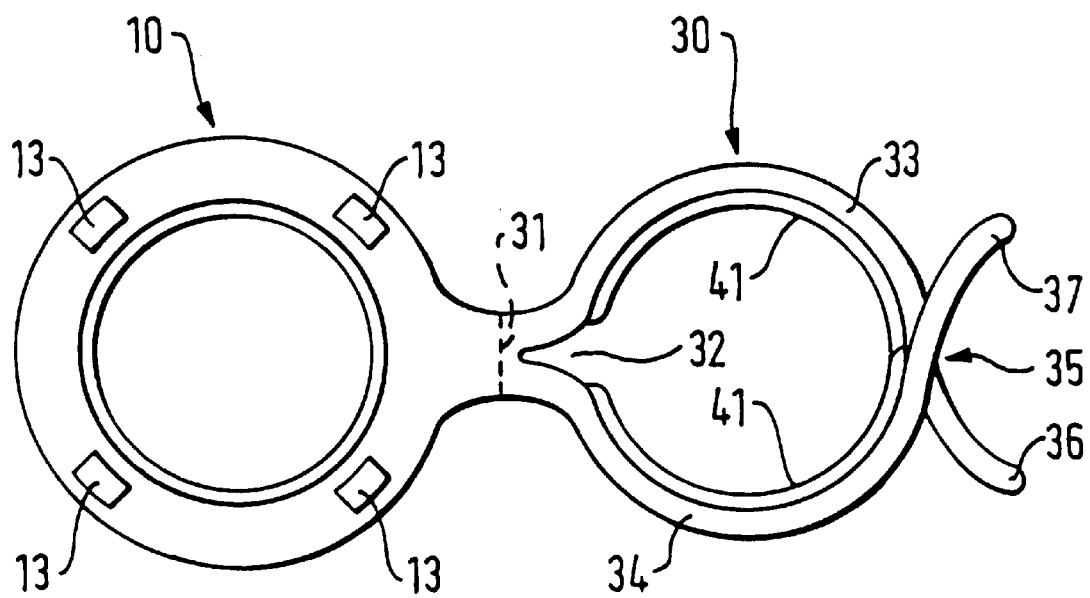
FIG. 2 is a plan view of the integral coupling member and locking ring prior to assembly.

In this embodiment, the locking ring 30 is formed integrally with the first coupling member 10, and is joined thereto by a hinge web 31. Adjacent to the web 31, the locking ring is formed with a notch 32 which provides a flexure point about which the limbs of the split ring 30 can be deformed. As best seen in FIG. 2, the locking ring includes two limbs 33 and 34, which extend in opposite directions from the notch 32, and cross over each other at the "split" region 35 diametrically opposite the notch 32. The region 35 corresponds to the "split" in the ring, which enables the limbs to be deformed to expand and contract the ring. The limbs 33 and 34 terminate after the cross-over with finger projections 36 and 37, respectively, which enable the ring to be expanded by finger pressure pushing the projecting ends 36 and 37 towards each other.

As best seen in FIGS. 1 and 3, each limb 33 and 34 consists of a radially flat portion 38 from which depends a radially outer rim 39. The radially inner edge of the that portion 38 is formed with a generally triangular engagement profile. which has a lead ramp surface 41, and a latch abutment surface 42 for engaging the second coupling member.

In this embodiment, the split ring 30 is moulded integrally with the first coupling member as a figure-of-eight shape. This provides a convenient way of reducing the individual part count of the coupling, and it can also simplify the assembly process. Before the coupling can be used, it is necessary to fold the locking ring 30 into its operative position in which it surrounds the cylindrical wall 12 of the first coupling member (as illustrated in FIGS. 1 and 3). The split ring 30 is retained in its operative position by a number of L-shaped retaining lugs 13 (four lugs in this embodiment) which project from the flange 11. Initially, in order to fit the split ring under the lugs 13, it is necessary to move the finger projections 36 and 37 of the ring horizontally away from each other, in order to reduce the diameter of the ring. Once the ring has passed under the lugs, the finger projections 36 and 37 can be released to allow the split ring 30 to expand back to its usual size.

With the split ring 30 in its operative position, the coupling can be assembled by advancing the second coupling member 20 on to the first coupling member (FIG.3). The lead in surface 24 of the second coupling member 20 bears progressively against the lead in surface 41 of the split ring 30 to push the limbs 33 and 34 of the split ring apart and allow the engagement profile of the second coupling member 20 to move past the engagement profile of the split ring 10. Thereafter, the split ring 30 springs back to its original shape (FIG. 3) and the abutment surface 42 of the split ring 30 engages behind the abutment surface 25 of the second coupling member 20, thereby latching the second coupling member 20 in position. The second connecting member 20 thus forms a snap fit against the first coupling member 10 without any need for the user to manipulate the split ring himself or herself.

To release the coupling, the user presses the projections 36 and 37 of the split ring towards each other, to move the limbs 33 and 34 apart, and thus expand the split ring 30. This action shifts the abutment surface 42 of the split ring 30 laterally clear of the abutment surface 25 of the second coupling member 20, and thus allows the second coupling member 20 to be separated from the first coupling member 10. It will be appreciated that the degree of movement of the split ring limbs 33 and 34 is greatest adjacent to the crossover (region 35) and, becomes progressively smaller towards the flexure point 32. The size of the abutment surface 42 of the split ring reflects this by being radially larger (i.e. projects further radially inwardly) adjacent to the crossover (and therefore needs greater movement to disengage the abutment surface 25 of the second coupling member), and becomes progressively radially smaller towards the flexure point 32 (such that less movement is required to disengage the abutment surface 25).

Figure 4:
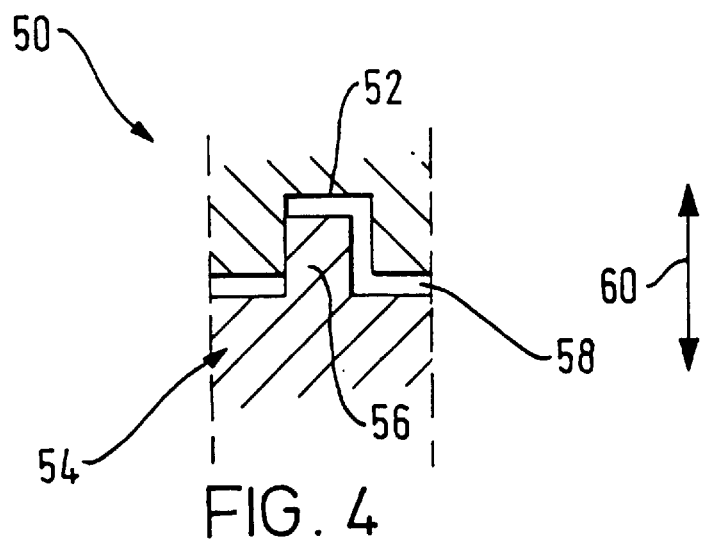
FIG. 4 is a schematic partial view of a mould for forming the first coupling member.

As can be seen in FIGS. 1 and 2, the flange 11 has apertures 14 which are co-extensive with the lugs 13. The apertures 14 do not have a function in use of the coupling, but instead are a consequence of the shape of the mould parts used to mould the flange 11 with the integral lugs 13. Typically, the mould parts for forming the lugs 13 will be as illustrated in FIG. 4. In this drawing, numeral 50 depicts an upper mould part with a recess 52, and numeral 54 depicts a lower mould part with a projection 56. The space 58 between the mould parts defines the moulded shape of the coupling member. It will be appreciated that an aperture in the flange under the lug allows the mould parts (and in particular the projection 56 under the lug) to be separated by a single movement in the direction indicated by arrow 60. Of course, if desired, the flange 11 could be moulded without apertures 14, but a more complicated mould would then be required (for example, with a part which can be rotated from under the lug 13 when the mould is to be opened).

Figure 5:
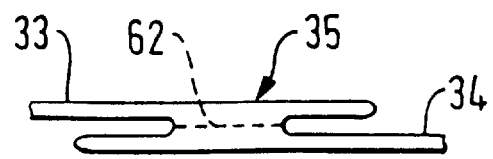
FIG. 5 is a schematic partial view of a detail of the split ring.

When moulding the split ring 30, it may be found convenient to mould the limbs 33 and 34 with a thin connecting web 62 at the cross-over 35, as illustrated in FIG. 5. The close spacing of the limbs 33 and 34 means that there is little room for a mould part to fit between the limbs at the cross-over, without causing the limbs to be moulded severely out of their correct planes. After moulding, the web 62 would need to be severed, before the split ring 30 was folded into its operative position. Of course, if it is desired to mould the limbs 33 and 34 without a web 62, then the mould may include a thin tongue which, in use, would fit between the limbs. However, such a thin mould part might be vulnerable to damage during the manufacturing process, and repair would then be expensive.

Although the split ring 30 is moulded integrally with the first coupling member in the above embodiment, it will be appreciated that this is not essential. In an alternative embodiment, the split ring 30 could be moulded separately, and fitted to the first coupling member in a similar manner to that described above.

It will also be appreciated that the invention, particularly as described in the preferred embodiments, can provide a coupling which is simple to use and to manufacture, but which can achieve positive engagement between the coupling parts over a large portion of the circumferential periphery of the coupling members.

In one aspect the lugs extending radially outside the split ring do not obstruct or otherwise interfere with the radially inner engagement surface of the split ring. This provides an extremely convenient (but not necessarily the only) way of increasing the available engagement areas around the periphery of the coupling members. The split ring and/or the removable coupling member may have substantially continuous interlocking or engagement surfaces around the periphery, or may have discrete tabs or tongues.

In another aspect, the substantially continuous engagement between the split ring and the second coupling member around the periphery of the second coupling member can provide excellent positive engagement, and can prevent unintended release of the coupling. At the same time, the coupling is nevertheless as easy to release manually as other couplings in this field.

In a further aspect, the moulding of the split ring integrally with the first coupling member provides a convenient way of reducing the individual part count, and of simplifying assembly.

While aspects of the invention believed to be of particular importance have been emphasised in the description and claims, the Applicant claims protection for any novel feature or combination of features described herein or illustrated in the drawings irrespective of whether emphasis has been placed thereon.

What is claimed is:

1. A coupling for a medical device comprising:
    first and second coupling members adapted for surrounding a body opening;
    a resilient split locking ring integral with and mounted on said first coupling member, said first and second coupling members being releasably securable together by said locking ring, said locking ring engaging said second coupling member substantially continuously around said periphery of said second coupling member so as to secure said coupling members together, said locking ring releasing said second coupling member when external forces are applied to expand said locking ring.

2. The coupling according to claim 1 wherein said split locking ring includes first and second limbs, each of said limbs having a continuous engagement portion for continuously contacting said periphery of said second coupling member.

3. The coupling according to claim 2 wherein each of said limbs includes an end portion proximate to said split and said end portions overlap each other.

4. The coupling according to claim 3 wherein said end portions include finger projections.

5. The coupling according to claim 1 wherein said split locking ring is retained on said first coupling member and said first coupling includes a retaining means for retaining said split locking ring thereon.

6. A coupling for a medical device comprising:
    first and second coupling members adapted for surrounding a body opening;
    a resilient split locking ring retained on said first coupling member, said first and second coupling members being releasably securable together by said locking ring,
    said first coupling member including retaining means radially outward of said locking ring for retaining said locking ring thereon, said retaining means permitting expansion of said locking ring when an external force is applied to said locking ring, said locking ring being expandable for releasing said second coupling member and permitting said coupling members to be seperated.

7. The coupling according to claim 6 wherein said retaining means includes at least one retaining lug projecting from said first coupling member.

8. The coupling according to claim 7 wherein said first coupling member includes a respective aperture associated with each retaining lug.

9. The coupling member according to claim 6 wherein said first coupling member and locking ring are integral.

10. The coupling according to claim 9 wherein said locking ring is joined to said first coupling member by a flexible web.

11. The coupling according to claim 10 wherein said flexible web has a hinge permitting folding of said locking ring onto said first coupling member.

12. The coupling according to claim 6 wherein at least one of said locking ring and second coupling member have a tapered surface to facilitate engagement of said locking ring with said second coupling member.

13. The coupling according to claim 7 wherein said first coupling member is attached to a medical grade adhesive pad.

14. The coupling according to claim 6 wherein said coupling is an ostomy coupling.

15. The coupling according to claim 14 wherein said first coupling member is a body-side coupling member and said second coupling member is a bag-side coupling member.

* * * * *